(12) United States Patent
Smith

(10) Patent No.: US 6,908,546 B2
(45) Date of Patent: Jun. 21, 2005

(54) APPARATUS AND METHOD FOR PRODUCING PURIFIED WATER HAVING MICROBIOLOGICAL PURITY

(75) Inventor: Steven D. Smith, Oakville (CA)

(73) Assignee: Bionomics LTD, Oakville (CA)

( * ) Notice: Subject to any disclaimer, the term of this patent is extended or adjusted under 35 U.S.C. 154(b) by 109 days.

(21) Appl. No.: 10/285,621

(22) Filed: Nov. 1, 2002

(65) Prior Publication Data

US 2003/0094406 A1 May 22, 2003

Related U.S. Application Data

(60) Provisional application No. 60/330,966, filed on Nov. 5, 2001.

(51) Int. Cl.$^7$ ............................................. B01D 61/12
(52) U.S. Cl. .................. 210/137; 210/87; 210/96.2; 210/149; 210/184; 210/192; 210/195.2; 210/201; 210/258; 210/321.65
(58) Field of Search ................. 210/87, 96.2, 137, 210/149, 182, 184, 192, 195.2, 196, 201, 258, 321.65, 321.69, 335, 637, 652, 739, 742, 774, 805

(56) References Cited

U.S. PATENT DOCUMENTS

| | | |
|---|---|---|
| 3,462,364 A | 8/1969 | Carlson |
| 4,574,049 A | 3/1986 | Pittner |
| 4,812,237 A | 3/1989 | Cawley et al. |
| 4,936,997 A | 6/1990 | Taniguchi et al. |
| 4,961,851 A | 10/1990 | Barbachano et al. |
| 5,032,265 A | 7/1991 | Jha et al. |
| 5,096,589 A | 3/1992 | Blind et al. |
| 5,156,739 A | 10/1992 | Dawson et al. |
| 5,207,916 A | 5/1993 | Goheen et al. |
| 5,259,972 A | 11/1993 | Miyamaru et al. |
| 5,306,427 A | 4/1994 | Xu |
| 5,338,456 A | 8/1994 | Stivers |
| 5,501,798 A | 3/1996 | Al-Samadi et al. |
| 5,512,178 A | 4/1996 | Dempo |
| 5,597,487 A | 1/1997 | Vogel et al. |
| 5,651,894 A | 7/1997 | Boyce et al. |
| 5,670,053 A | 9/1997 | Collentro et al. |
| 5,766,479 A | 6/1998 | Collentro et al. |
| 5,925,240 A * | 7/1999 | Wilkins et al. ............... 210/88 |
| 5,925,255 A | 7/1999 | Mukhopadhyay |
| 5,997,745 A * | 12/1999 | Tonelli et al. ............... 210/652 |
| 6,074,551 A * | 6/2000 | Jones et al. .................. 210/106 |
| 6,080,316 A | 6/2000 | Tonelli et al. |
| 6,099,799 A | 8/2000 | Anderson |
| 6,113,797 A | 9/2000 | Al-Samadi |
| 6,120,689 A | 9/2000 | Tonelli et al. |
| 6,126,834 A | 10/2000 | Tonelli et al. |
| 6,129,845 A | 10/2000 | Kim et al. |

(Continued)

FOREIGN PATENT DOCUMENTS

| | | |
|---|---|---|
| DE | 31 06 772 A | 9/1982 |
| JP | 59042007 | 6/1984 |

*Primary Examiner*—Joseph Drodge
(74) *Attorney, Agent, or Firm*—Ingrid E. Schmidt

(57) ABSTRACT

A process is provided to produce water that will meet the specifications of the United States Pharmacopeia Inc. for Purified Water and Water for Injection, and water for dialysis as circumscribed by the American Association for Advancement of Medical Instrumentation (AAMI). The system has no storage tanks where stagnant water will be fouled by biofilm colonizing the tank surface. Water is circulated throughout the purification system and drawn as required, on demand. The water is purified and used immediately or recycled and repurified to ensure quality. Sanitation of the purification system, maintaining microbiological purity and cleaning is done by controlling the pH so that it is normally acidic by maintaining a high carbon dioxide concentration in solution, the carbon dioxide being allowed to pass into the permeate from a reverse osmosis membrane assembly used to purify the water.

28 Claims, 12 Drawing Sheets

U.S. PATENT DOCUMENTS

| | | |
|---|---|---|
| 6,180,012 B1 | 1/2001 | Rongved |
| 6,190,556 B1 * | 2/2001 | Uhlinger .................... 210/636 |
| 6,228,255 B1 * | 5/2001 | Peterson et al. .............. 210/90 |
| 6,235,199 B1 * | 5/2001 | Peterson et al. ............ 210/646 |
| 6,251,279 B1 * | 6/2001 | Peterson et al. ............ 210/636 |
| 6,258,278 B1 | 7/2001 | Tonelli et al. |
| 6,267,891 B1 | 7/2001 | Tonelli et al. |
| 6,607,668 B2 * | 8/2003 | Rela ........................ 210/321.6 |

* cited by examiner

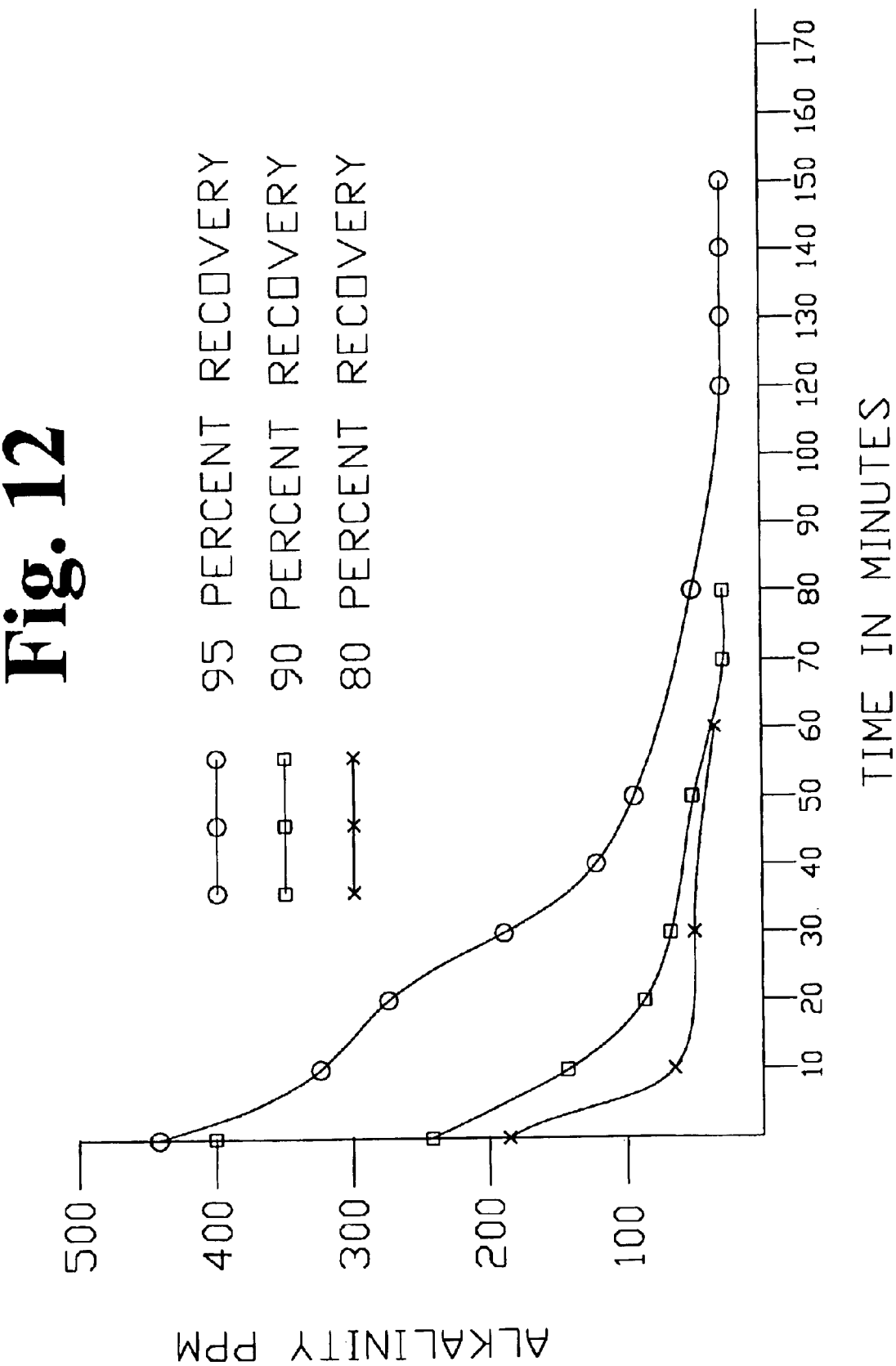

APPARATUS AND METHOD FOR PRODUCING PURIFIED WATER HAVING MICROBIOLOGICAL PURITY

FIELD OF THE INVENTION

This invention relates to a water purification system which incorporates a double pass reverse osmosis membrane assembly for filtering pretreated water and to a method of operating such a system.

BACKGROUND OF THE INVENTION

A typical prior art water purification system is illustrated in FIG. 1. Feed water is pretreated at 20 and fed to a first storage tank 22 prior to heating in a heat exchanger 24 to a specified membrane operating temperature, typically 25° C. Pre-treatment equipment, which is based on the potable source water quality, typically comprises a multimedia filter to remove particulates, a softener to remove mineral scale, a carbon filter to remove chlorine/chloramines or a chemical injection system using a bisulphite type chemical, possibly a UV station for bacteria kill, and prefilters (1–10 μm) to remove particulates prior to the water entering the reverse osmosis system. After some chemical additions 26, the water is fed to a reverse osmosis membrane assembly 28 and the purified water is treated with ultraviolet light in a first UV station 30, deionized at deionization station 32, treated in a second UV station 34, and passed through a first sterilizing filter 36 before being fed to a second storage tank 38. Water is drawn from the second storage tank 38 at various points of use generally indicated by reference numeral 40 after appropriate treatment including a third UV station 42, a second sterilizing filter 44 and a second heat exchanger 46 to maintain ambient temperatures. Water from the second storage tank 38 is also recirculated through an ozonation system 48 with a pump 50 to reduce bacterial growth. An alternative microbial control design may include a heat exchanger for periodic heat sanitization.

It will be seen from FIG. 1 that excess reject water from the reverse osmosis membrane assembly 28 is drawn through pump 52 to be recirculated to the reverse osmosis membrane assembly 28 while the balance of the reject water is sent to drain. Operation of the system is controlled with a central programmed logic controller (PLC) indicated at 54.

The system is quite complicated in that it has many technologies to monitor and control. The majority of these types of systems are custom built due to the variability of source water and the intricacies of different production demands. With the current approach in the industry, a human operator cannot control and monitor all of the variables to a satisfactory level. This necessitates an expensive PLC control system. The PLC system is also custom designed due to the above considerations. The complexity of this system dictates long lead times for delivery of the equipment. Once the equipment is placed at location, a long process is employed to adjust all of the technologies in order to maintain the desired water quality. Regular cleaning and sanitization must be performed on the equipment to ensure microbial integrity. Due to the variety and complexity of equipment employed, the maintenance is high. If one piece of equipment fails, the water production process ceases. Depending on the location of the failure, it may dictate sanitization of the equipment or system prior to placing it back into service. This represents lost production time. The complexity of the equipment dictates a thorough investigation and testing prior to releasing the system for production.

High-energy input is required to temper the water (increase to 20–25° C.) to feed the system and meet reverse osmosis membrane specifications. In addition, high energy consumption and labour are required to maintain the system within specifications. The percent of water recovery or yield is low, being typically 60 to 75 percent of the system's demand.

Microorganisms, specifically bacteria, form biofilm, which is an extra-cellular organic polymer (polysaccharide in nature). Biofilm can also incorporate divalent metal ions that can form a lattice structure consisting of both organic and inorganic mass. This structure protects the organisms from sanitization and cleaning chemicals. Once this formation develops within a system it is very difficult to remove.

The storage tank is a grower of microorganisms unless an ozonation system is applied. This option is capital intensive and has associated operating and maintenance expenses. In addition ozone is a hazardous substance requiring appropriate safety precautions. Ozone is an added substance to the purified water in order to control the microbial integrity. In systems not employing ozone, the microbes will settle onto the tank surface, due to little movement of water (no velocity), and produce biofilm. Free-floating (planktonic) organisms will reproduce and contaminate the distribution system. Biofilm will protect the organisms from chemical sanitization and allow them to reproduce. Chemical sanitization will be reduced in effectiveness. Systems employing heat sanitization are capital and energy intensive and do not remove biofilm.

The typical prior art water purification system is not designed to prevent the growth of microbes. The approach has been to allow the microbial population to increase to a certain range in numbers, then to clean and/or sanitize the system, thus reducing the microbial population. Microbiological procedures require an incubation period of approximately two days or longer prior to enumeration. The delay in results can have the system out of specification for microbial numbers prior to cleaning and sanitizing. Alternatively, a high frequency scheduled cleaning and/or sanitization regimen is implemented to reduce the possibility of the microbial numbers exceeding specification. This approach is labour and energy intensive and prevents the use of the system while the procedures are being conducted. The design of the prior art does not inherently reduce or prevent the growth of microorganisms during the water purification process.

Various attempts to regulate the conductivity of high purity product water have been described in the prior art. A major problem identified in a double pass reverse osmosis system is the difficulty in rejecting gases such a carbon dioxide. Carbon dioxide present in the feed water will pass through the first pass membranes and the second pass membranes forming carbonic acid and the corresponding equilibrium equation products which result in increased conductivity of the product water. This phenomenon is viewed negatively by the prior art since the increase in conductivity is perceived as decreasing the quality.

The following equations express the carbonic acid formation and equilibrium:

Carbonic acid formation

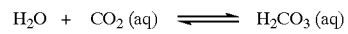

Carbonic acid equilibrium

It is noted that the formulas were not reproduced in the form in which they were filed. The arrows are missing. If necessary, they may be replaced by equal signs.

Methods attempted for removing carbon dioxide are described in several US patents some of which are discussed below. In U.S. Pat. No. 4,574,049 and U.S. Pat. No. 5,997,745 an alkaline agent is added between the first and second pass to convert the carbon dioxide gas to carbonate which is rejected by the second pass membranes. Addition of an alkaline is used prior to the first pass in conjunction with an acid to the second pass with or without a gas liquid separation module in U.S. Pat. No. 5,766,479. Gas removal by hydrophobic gas permeable membrane contactors is described in patents U.S. Pat. No. 5,156,739 and U.S. Pat. No. 5,670,053. Removal by a forced draft decarbonator and a vacuum degasifier is explained in U.S. Pat. No. 5,338,456 and U.S. Pat. No. 5,250,183. Removal by a forced/induced draft decarbonator before or after a two pass reverse osmosis system is disclosed in U.S. Pat. No. 5,925,255. One solution described in U.S. Pat. No. 6,258,278 is to first treat feed water with a strong base anion resin and subsequently removing carbon dioxide in order to maintain a high pH of 6 to 9.5. U.S. Pat. No. 6,080,316 and U.S. Pat. No. 6,126,834 describe the use of caustic injections to adjust the pH of the infeed water that is controlled by a PLC based on resistivity measurements of the product water. These patents plus others describe a removal process for $CO_2$ or methods of preventing the $CO_2$ from ending up in the product water. These patents view the increase in conductivity due to the presence of $CO_2$ in the product water negatively.

Prior art water purification systems are typically designed to produce the purified water at a defined rate. It is usually based on the maximum required water volume demand during a period of time (hour, shift, day or number of dialysis machines, etc.). To this rate a storage tank can be sized to provide this maximum rate with a minimum buffer volume of approximately 20 percent. The systems cannot vary their production rate by more than a few percentages of the original designed rate.

The object of the invention is to provide a better means of producing water that will meet the specifications of Purified Water and Water for Injection as defined by the United States Pharmacopeia Convention Inc. (as defined but not limited to the current edition XXV) and water for dialysis as defined by the American Association for Advancement of Medical Instrumentation (AAMI).

The invention provides a means of purifying water that supplies the purified water to the point or points of use to allow the water to be drawn immediately on demand. The water that is not used immediately is recycled and repurified to ensure continuous quality.

Another object of the invention is to provide purified water directly to the point or points of use without the requirement for a storage and distribution system. The means of providing the water directly to the point of use is an integral part of the purification process.

The invention's objective is to provide purified water having very low microbial counts. Still another object of the invention is to provide a means of purifying water, which is not conducive to growth of microorganisms within the purification process.

In addition, the object of the invention is to provide a means of removing microorganisms that may grow within the purification process.

The object of the invention is also to provide variable production rates to meet variable demand requirements. In addition this saves energy and water.

It is another object of the invention to provide a means to self-clean the purification system of mineral scale and microorganisms.

Still another object of the invention is to allow the system to self-purge itself of purified water that does not meet the conductivity or temperature parameters.

The objects of this invention include providing a water purification system, which can be operated to produce high purity water at a reduced capital cost investment and with lower operating costs.

SUMMARY OF THE INVENTION

Sanitation and cleaning of the system is done by controlling the pH so that it is normally acidic in contrast to prior art systems and this is done naturally without any acid additions by maintaining a high carbon dioxide concentration in solution, the carbon dioxide being concentrated into the permeate from a reverse osmosis membrane assembly used to purify the water. To increase pH to neutral values for end uses, or reduce the conductivity of the purified water by that contributed by the $CO_2$, a base may be added or carbon dioxide may be allowed to escape from solution.

BRIEF DESCRIPTION OF THE DRAWINGS

In order to better understand the invention, illustrative embodiments of a water purification system are described below with reference to the accompanying drawings, in which:

FIG. 12 is a graph showing the reduction in alkalinity over time of the water circulating onto first pass reverse osmosis membranes when the system is operated in idle or circulation mode.

DESCRIPTION OF THE INVENTION

Figure 1:
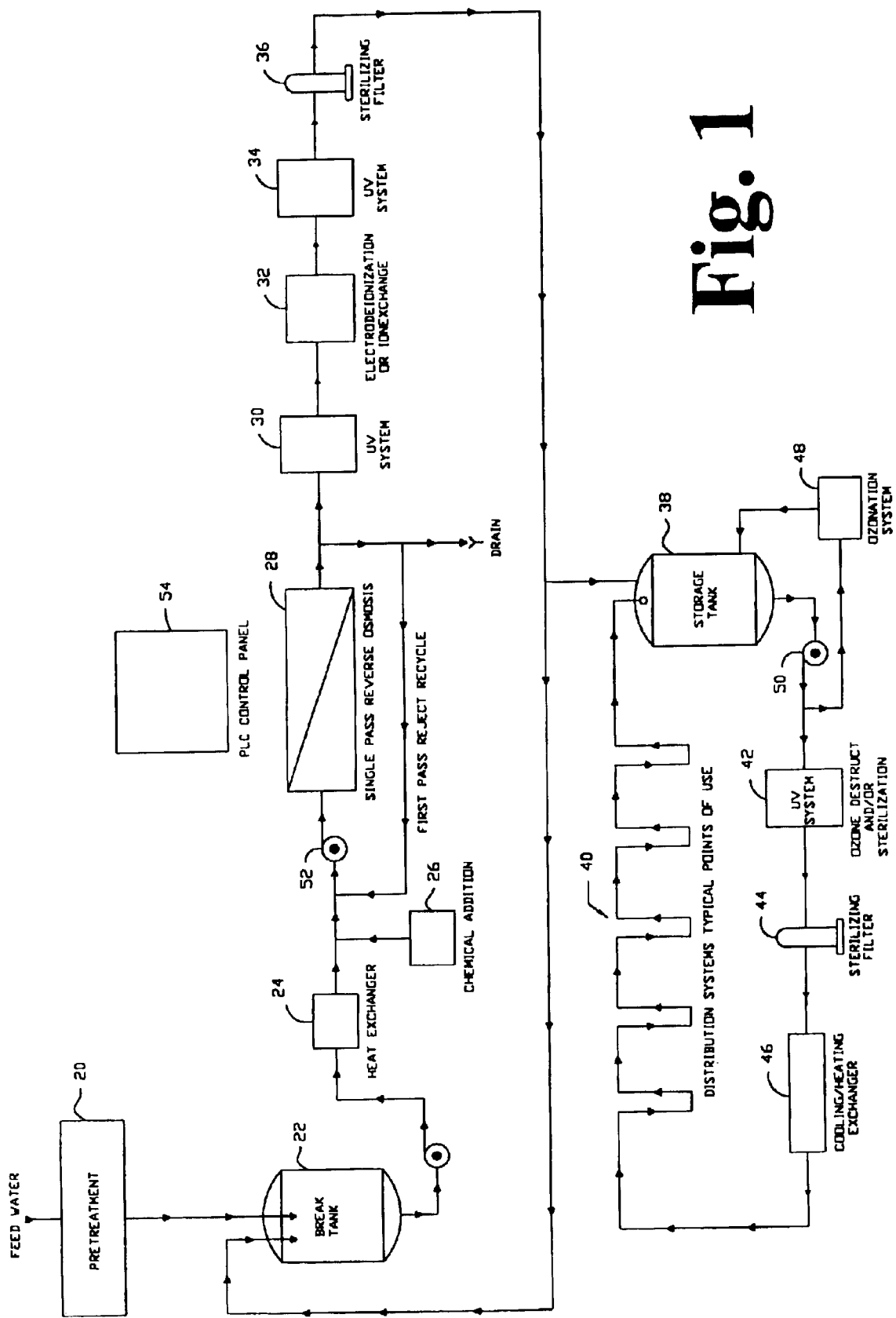
FIG. 1 is a schematic flow diagram showing a typical prior art water purification system including a single pass reverse osmosis membrane assembly and a distribution system including a storage tank.
Figure 2:
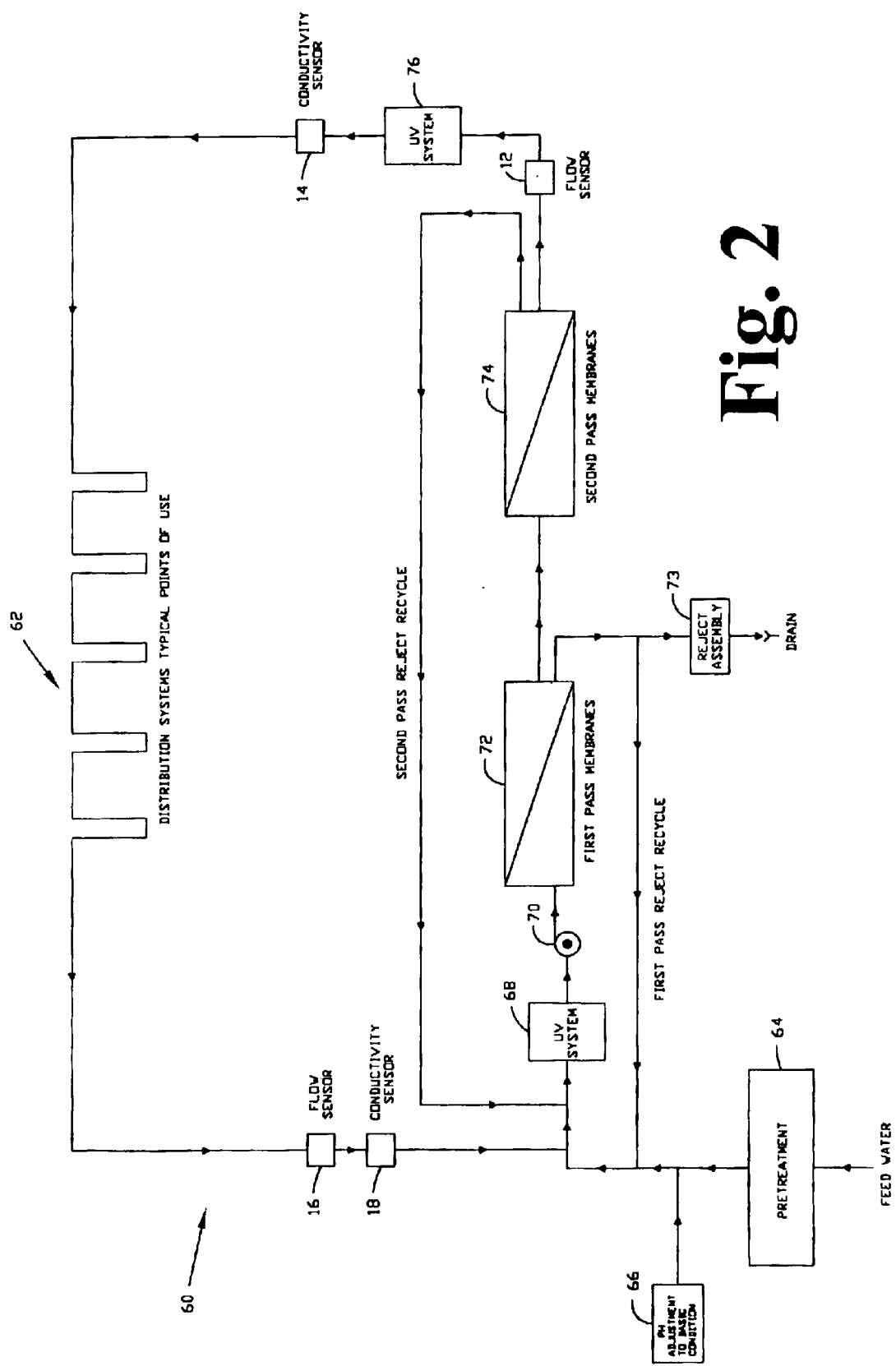
FIG. 2 is a schematic flow diagram showing a water purification system according to the invention and including a double pass reverse osmosis membrane assembly with points of use and operating at a cold temperature.

In its simplest embodiment, a water purification system in accordance with the invention and indicated generally by reference numeral 60 in FIG. 2, has purified water (permeate) drawn directly from the purification process at points of use generally indicated by reference numeral 62 without any previous storage in a tank or locations where water will stagnate and be susceptible to bacterial growth.

The feed water is fed to appropriate pretreatment at 64 and optionally has its pH adjusted to a basic condition through the addition of sodium hydroxide (NaOH) at 66 whereafter it is passed through a first ultraviolet radiation treatment station 68 prior to being pumped with a variable speed pump 70 to a first reverse osmosis membrane assembly 72.

The permeate from the first reverse osmosis membrane assembly 72 is fed to a second reverse osmosis membrane assembly 74 and its permeate is passed through a second ultraviolet radiation treatment station 76 before being drawn at various points of use 62, as required. Excess permeate water not used at the points of use 62, and a major portion of the reject water from both the first reverse osmosis membrane assembly 72, and all of the reject water from the second reverse osmosis membrane assembly 74 is recycled through the first reverse osmosis membrane assembly 72 after passing through the first ultraviolet radiation treatment station 68. The ultraviolet radiation treatment sterilizer station 68 is used to reduce the incoming microbial load from the pretreated source water and circulation water prior to entry into the first pass reverse osmosis membrane assembly 72 while the second ultraviolet radiation treatment sterilizer station 76 is used to kill organisms that will eventually grow on the downstream side of the membrane of the second reverse osmosis membrane assembly 74.

The invention is characterized by the absence of a storage tank, which would otherwise provide fertile ground for microbial growth and contamination of permeate. This is rendered possible by appropriate design selection of the supply capacity to maintain an approximate minimum velocity of 3 ft/sec. (1 meter/sec.) and usually 5 to 7 ft/sec (2 meters/sec.) and by operating the system to keep the permeate in circulation. A minimum velocity to maintain a continuous turbulent flow condition within the piping is known to be approximately 3 ft/sec (1 meter/sec). Conveniently, maintaining a minimum turbulent velocity will reduce the growth of microorganisms and prevent the formation of biofilm on the walls of the point of use piping.

System production rate is designed based on the expected draw off demand and the appropriate serpentine pipe size with the corresponding velocity. Assuming an average pipe velocity of 6 ft/sec., systems can be built with common pipe sizes as follows:

| | |
|---|---|
| 1/8" pipe (3.0 mm) | 0.2 US gpm (0.85 Lpm) |
| 3/16" pipe (4.8 mm) | 0.5 US gpm (2.1 Lpm) |
| 1/4" pipe (6.2 mm) | 0.9 US gpm (3.8 Lpm) |
| 3/8" pipe (9.6 mm) | 2.0 US gpm (8.5 Lpm) |
| 1/2" pipe (12.5 mm) | 3.6 US gpm (15.0 Lpm) |
| 3/4" pipe (19.0 mm) | 8.0 US gpm (34.0 Lpm) |
| 1.0" pipe (25.4 mm) | 14.5 US gpm 60.0 Lpm) |
| 1.25" pipe (32.0 mm) | 23.0 US gpm (95.0 Lpm) |
| 1.5" pipe (36.0 mm) | 32.0 US gpm (135.0 Lpm) |
| 2.0" pipe (51.0 mm) | 60.0 US gpm (240 Lpm) |
| 2.5" pipe (64.0 mm) | 90.0 US gpm (380 Lpm) |
| 3.0" pipe (76.0 mm) | 130 US gpm (550 Lpm) |
| 3.5" pipe (90.0 mm) | 180 US gpm (750 Lpm) |
| 4.0" pipe (100 mm) | 230 US gpm (950 Lpm) |
| Etc. | |

The required maximum demand at the points of use 62 would first be found. As an example, 30 US gpm. (120 Lpm) are required at the point of use on a continuous basis. In order to maintain an approximate minimum velocity of around 3 ft./sec. (1 meter/sec.) on the loop return, a system would have to produce 2 times the continuous amount required at the point of use. This would dictate a 2" (51 mm) distribution loop and an average production rate of around 60 US gpm. (240 Lpm).

The invention is typically designed with a surface area of the first pass having 1.5 to a maximum of 3 times the surface area of the second pass membranes, but most usually 2 times. Ideally the first pass membrane flux (flow rate per unit surface area per unit time) is in a range of 10 to 20 gallons per square foot per day (406 to 812 litres per square meter per day). The water feed flow to the first pass membranes is typically a minimum of 3 times the average production rate from the second pass reverse osmosis assembly 74 to provide high cross flow that will reduce fouling of the membranes.

EXAMPLE

A phenomenon was discovered that produced two effects. The system is generally run in two different modes of operation. The "production mode" is defined when water is being drawn from the system. The "circulation or idle mode" of operation occurs when no water is being drawn off at the points of use. All water, except for reject water, is recirculated and repurified. A system of the same design as shown in FIG. 2 was operated for 30 minutes in production mode (water drawn from the system) under different product recovery levels (80%, 90% 95%) and then placed on idle or circulation mode having the same recovery levels. Osmonics Inc. manufactured the polyamide membranes, model designation AK8040, used in the system.

The tap water feed was first softened and then dechlorinated, using a bisulfite injection system, prior to a 5.0-micron cartridge filter system. The feed water had a pH of 7.2, a conductivity of 340 μS/cm. and alkalinity of 119 ppm. (as $CaCO_3$).

Figure 10:
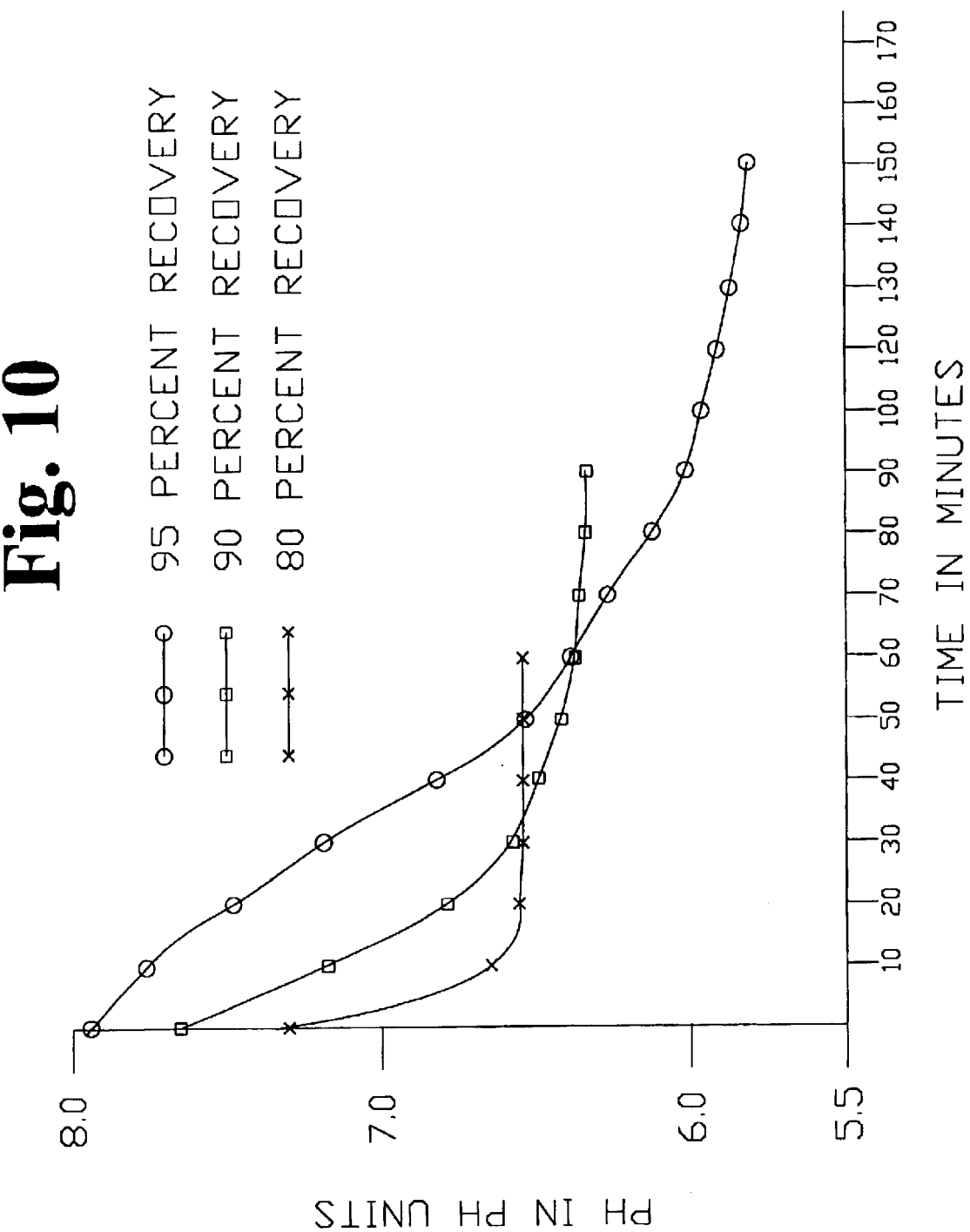
FIG. 10 is a graph showing the reduction in pH over time of the water circulating onto first pass reverse osmosis membranes when the system is operated in idle or circulation mode.
Figure 11:
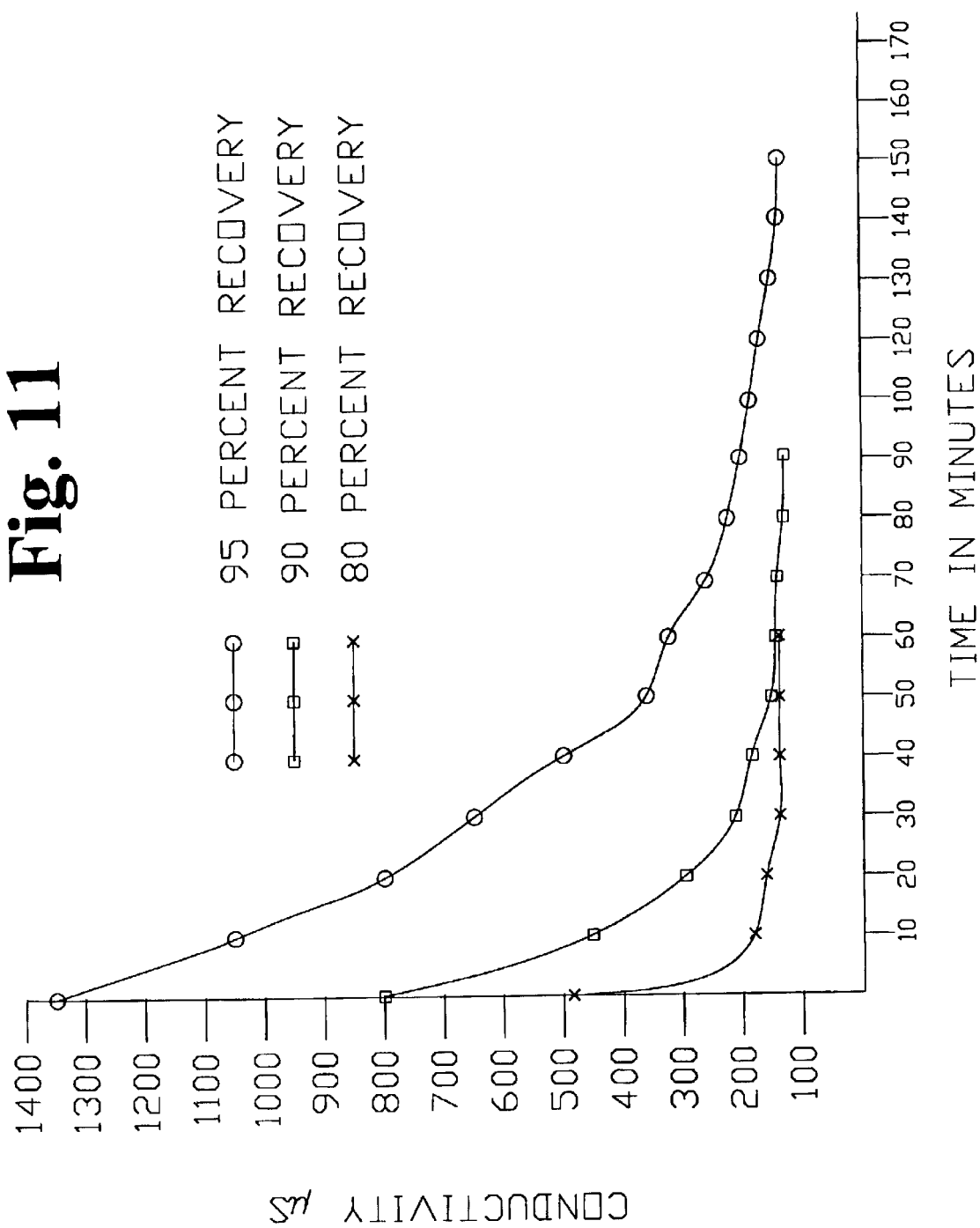
FIG. 11 is a graph showing the reduction in conductivity over time of the water circulating onto first pass reverse osmosis membranes when the system is operated in idle or circulation mode.

After a 30 minute production stabilization period, the circulating water fed to the first pass membranes was sampled for pH, conductivity and alkalinity, as a function of time for each product recovery level. FIGS. 10, 11 and 12 show the effect of circulation mode over time for the reduction in pH, conductivity and alkalinity respectively.

The conductivity of the circulation water, which consisted of the new water entering the system, the majority of the water recycled from the reject of the first pass, all of the reject water from the second pass, and all of the product water, dropped to less than one half of the conductivity of the incoming feed water. In addition a second effect was observed that produced a corresponding reduction in pH (see FIG. 10) with the reduction in conductivity. The pH dropped to below 6.5 when the recirculating water's conductivity dropped below one half of the feed water conductivity. The rate of the effect to demonstrate itself was in proportion to the total dissolved solids in the recirculated water. The significant reduction in all three parameters from the production mode values to well below the tap feed water values demonstrates the self-cleaning ability of the invention when operated in circulation mode.

The second pass reverse osmosis product water in all three operating conditions, that is, at product recovery levels of 95%, 90% and 80% consistently had a pH of below 5.5.

The invention is further characterized by, the reverse osmosis membranes having the well known property of producing a permeate with dissolved carbon dioxide content. The water purification system 60 is operated to produce an acidic permeate during normal production and times when no water is drawn from the points of use at 62 (idle mode), the acidity in the permeate, and in the system, being increased in part by allowing the pH to decrease as a result of pressurizing the water to maintain carbon dioxide in solution.

An acidic condition is desirable to remove the inorganic fouling fraction from membrane surfaces and to reduce scaling. Minerals such as calcium and magnesium carbonates which are dissolved and maintained in solution are sent to drain. In addition, the high level of acid within the system will permeate the membranes and be distributed through the system sanitizing the whole reverse osmosis system and point of use piping. Microorganisms have an optimum pH range in which they grow. This range is ideally between pH 6.5 to 7.5. As the pH drifts above or below these values, the alkalinity or acidity becomes toxic to the organisms. Organisms that are commonly found in source water (i.e. Pseudomonades) will not grow in acid conditions. In fact, acid conditions at and below pH 5.5 will kill acid sensitive organisms. The area of most concern in the reverse osmosis system is the product spacer screens of the second pass. Reverse osmosis membrane manufacturers do not make claims for sterility of the permeate water. They do state that there will be >99% rejection of microorganisms. The first pass in theory will remove >2 logs and the second pass will reject approximately 2 logs. The problem that has been observed is that the organisms eventually culture and those, which pass the first stage, infect the second stage. The organisms that grow on the second stage will eventually pass into the permeate of the second stage. Due to the inherent design construction of reverse osmosis membranes, the organisms start to culture in the second pass permeate side of the membranes. This is the major area of infection that directly contributes to the contamination of the product water. The organisms then slough off into the water and infect the downstream piping. In this invention, the high acidic conditions after the second pass, approximately pH 5.5 or below, effectively prevent the growth of or kill the organisms that have cultured in the second pass permeate spacers.

The invention thus allows for self-sanitization without peripheral stations for additional, sterilizing filters, and ozonation systems typical of the prior art. The invention can maintain an undesirable state to prevent microorganisms from growing and to clean mineral deposits when the system is not called upon to produce water for a process. The ability of this invention to produce low pH product water, particularly on the permeate side of the second pass, will kill acid sensitive organisms and prevent growth of microorganisms. The invention operated under these conditions is the most desirable.

The ability to reduce the conductivity and pH of the water in circulation mode will allow for operation of the invention without the use of a water softener in the pretreatment. A softener would not be required in pretreatment for removal of water hardness under conditions where the feed water is low to moderately hard and the system is not called upon to produce water for a process on a continuous bases. The circulation or idle mode will clean the membrane of material collected during the production mode.

The current state of the membrane art has developed two different types of membranes: cellulose acetate (CA) and thin film composite (TFC) which are commonly employed in water purification. Each membrane has its strengths and weaknesses. The CA membrane is not susceptible to chlorine but is susceptible to basic conditions (high pH). The TFC membranes are not susceptible to high pH but are susceptible to chlorine. TFC membranes require chlorine removal—usually carbon or bisulphate injection. Carbon grows bacteria that will contaminate the system. If carbon is used, a provision is made to sanitize it with heat (hot water or steam increasing the cost of equipment and operating costs). Both membranes will tolerate low pH. A system using CA membranes would not require any form of pretreatment (no chlorine removal, no softening/acid/anti-scale injection) other than a mechanical cartridge type filter for particulate removal. A system using TFC type membranes would not require softening/acid injection/anti-scale but would require a provision for particulate and halogen removal. The TFC system could incorporate a chlorine destruct ultraviolet system to destroy chlorine (i.e. as produced by Aquafine or Trojan). The ultraviolet system would be placed just prior to the pump. The acidified water would assist in preventing mineral scale build-up on the quartz sleeves forming part of the ultraviolet system and which would affect the overall intensity of the ultraviolet radiation into the water. The ultraviolet radiation would also inactivate microorganisms that would be introduced in the feed water and potentially any that would be derived from the distribution system.

Heat exchangers to temper the feed water are not required for operation of this device. It is well known in the art of membrane water purification that as the temperature decreases the water viscosity increases and visa versa. The water viscosity directly affects the production rate of the reverse osmosis membranes. This can be as-high as a decrease in production capacity of >2% for every degree C. below 25° C. (25° C. is the membrane manufacturers standard flux rating temperature). At 5° C. the decrease in production rate can exceed 40% at the same specified pressure. In decreasing water temperatures, to maintain the same production rate, a corresponding increase in pressure is required. Water purification systems incorporating the invention do not use heat exchangers to temper water for the following reasons:

a. The membrane surface area in the design is increased to account for the production loss due to temperature.

b. It is desirable from a microbiological point of view to maintain a low temperature within the reverse osmosis and point of use and return piping to decrease the rate of growth of microorganisms.

c. A significant amount of energy can be saved by not tempering the water to 25° C.

The selection of reverse osmosis membranes and the process design of this invention preclude the need to temper the feed water. Membrane manufacturers modelling programs (i.e. Osmonics and Dow) will determine the best membrane selection for the ionic quality of the product water as it relates to the temperature of the feed water. A combination of membrane surface area and types can be employed to obtain the desired ionic quality and production rate. Heating energy represents a significant contribution to operating costs on prior art systems and can be as high as 50% during the winter months in northern climates.

Cooling exchangers are not normally employed in the design of this device. The water rejected from the first pass membranes and the water drawn at points of use acts as a heat sink for the system. Typically an increase of approximately a couple of degrees Celsius is observed between the infeed temperature and the product water returning from the use points. The heat build up within the system is based on the percent recovery, the draw off volume with cycle rate, and the membranes' maximum allowable operating temperature. Storage based systems build up heat from the pump and frictional losses within the distribution system. These systems employ cooling exchangers to maintain the temperature usually between 20–25° C., which is an ideal temperature for microbial growth. Under conditions of high recovery rates where source waters are inherently warm (tropical climates) a cooling exchanger could be employed with this invention. The location of the exchanger would be on the infeed, or in the circulation system within the device (prior to the pump and membranes), thus insuring lower capital cost since sanitary design is not necessary as with storage based systems.

It will be appreciated that high temperature product water or water that does not meet the conductivity specification will be automatically sent to drain. A normal reject rate is established in the system usually between 2 and 50% of the product production rate or 50–98% recovery. The water rejected to drain and product water drawn off act as heat sinks to dump the heat from the system that is built up due to pump horsepower and friction. A conductivity/temperature sensor 14, 18 measures product water quality on either the purified water supply line to the points of use 62 (product line) or on the return piping back to the reverse osmosis membrane assembly 72. If water exceeds either or both limits, an automatic valve forming part of a reject assembly 73 on the reject line opens to dump additional water to drain. This acts to purge the system of water which in not within specification. After the quality has been re-established, the automatic valve 73 closes to return the system to normal operating conditions.

A variable frequency drive (VFD) is associated with the motor controlling pump 70 and used for hydraulic control within the system. A flow meter with sensor 12, 16 on the product water line and/or point of use return line will monitor product flow rate. The sensor or sensors (12, 16) will transmit a signal to the variable frequency drive to increase or decrease the speed of the pump motor 70. The VFD will allow for operation of a water purification system according to the invention from a minimum of 3 feet per second (1 meter per second) to a maximum recommended velocity of 9 feet per second (2.7 meters per second). It will be understood that the system is designed for continuous operation so that water is never left stagnant. Exceeding 10 feet per second (3.0 meters per second) can produce water hammer within the system. This equates to a production rate as low as 50% of the average designed rate to a maximum of 150% of the average designed rate. The VFD is employed for different operating conditions and reasons:

a) During draw down the loop return flow sensor 16 will detect a decrease in flow. This will speed up the revolutions per minute (RPM) of the pump 70 to increase the applied pressure on the reverse osmosis membrane assemblies 72, 74, which in turn will produce more water to compensate for the draw down volume. This also maintains the minimum requirement of 3 feet per second (1 meter per second) velocity in the return line.

b) In northern climates, water sources can vary in temperature depending upon the season particularly if the source water is from a surface source (lake, river or reservoir). The VFD will automatically control the production rate based on product flow, irrespective of temperature and water viscosity. Temperature variation will not affect production rate.

c) Temporary adjustments can be made for increased or decreased water demand. Production rates can be modulated within defined parameters. A manual setting of the VFD can set the production rate from as low as 50% of the pumps RPM range to 100% of its range, which would produce a production, range of from 50% to 150% of the designed average production rate.

d) Maintaining the velocity in the point of use piping of ideally 3 feet per second (1 meter per second) but not to exceed 6 feet per second (2 meters per second) during idling times, when no water is drawn from the system, will reduce water consumption and power requirements to save energy. It also reduces the possibility of microbes from settling onto the piping wall that will eventually form biofilm and contaminate the system.

e) In the case of a power failure, the VSD will soft start the system. When power is restored, the pump 70 will initiate a slow ramp up to bring the system up to operating specifications increasing the RPM to operational speed. This prevents hydraulic shocks, which reduces ware and tear on the system and associated point of use equipment. The system will be self-regulating to return itself to producing the desired water quality and quantity.

f) Used during clean in place (CIP) of the system. The frequency drive would be set at around 50 percent of the motor's maximum frequency, in addition the back pressure regulating valves would be opened on the recirculation lines. This produces a good velocity of flow within the system at low pressures. During CIP, it is desirable to maintain a high velocity across the membranes at low pressures to lift the deposited material off the membrane surface. The cleaning chemicals can be dosed into the system with appropriate chemical neutralization on the first pass reject.

Energy efficiency can be realized with the use of submersible pumps. The water being pumped cools the motor. This heat energy is picked up by the water from the pump motor and friction through the distribution system and assists in reducing water viscosity, which increases production rate at a specified pressure. This in turn saves energy costs on pump horsepower.

Sanitary design considerations are used throughout. At least one pump 70 is used to apply pressure to the first pass. The residual pressure from the first pass is used to feed the second pass. This is a more sanitary design than a pump for the first pass and a second pump for the second pass. In addition, the pump 70 is located on the contaminated side of the purification process, which is upstream of the first set of membranes. If a pump 70 has to be replaced, sanitization of the process and point of use 62 piping would not be required as in the typical prior art. In addition a spare pump could be added to the system, swing elbows from the existing pump could be rotated over to the second pump very quickly to reduce down time.

The invention can be operated to regulate itself to maintain product water quality and quantity with only 2 sensors, a combination conductivity/temperature sensor (14, 18) and a flow sensor (12, 16). No other controls are required to allow the system to self regulate. The flow sensor (12, 16) will provide the feedback for the VFD to maintain the velocity and production rate. The conductivity/temperature sensor (14, 18) will regulate the automatic valve located on the reject assembly 73 to send high temperature or conductivity water to drain which will clear the system quickly and maintain the hydraulic balance.

The system can be operated with very simple controls. A programmed logic controller (PLC) or proprietary control systems are not required for operation.

The invention is adaptable to various source water qualities up to approximately 2,000 mg/L of total dissolved solids (TDS) based on the existing membrane art. Adjustments can be made to the percent recovery on the system to ensure the final product water quality (from 50% to 98%). In addition, choices can be made of different membranes having different rejection characteristic to assist in the final water quality. As membrane technology advances, higher rejection membranes can be employed to use this device on even higher TDS source water. In cases where the source water exceeds recommended operating guidelines, as specified by the membrane manufacturers, appropriate pre-treatment, as designed by those skilled in the art of water purification, can be employed.

Typical two pass reverse osmosis systems in the prior art are usually designed to run with a 50–60% overall recovery. The typical recovery for this design is 80 to 98% during the production mode. The percent recovery would be dependant on source water temperature and total dissolved solids level.

Where system recovery, in the production mode, is below 90%, it can be increased to 90–98% when operated in circulation or idle mode by using an additional automated valve on the reject assembly 73. The automated valve would close once the idle mode has been initiated to decrease the amount of water sent as reject water.

Conveniently, the acidified water circulating over the first pass membranes 72 during circulation or idle mode also assists in the reduction of chlorine and chloramines.

Prior art systems have employed a process called direct feed that does not use a storage tank. Essentially this consists of a distribution pipe from the outlet of the purification process that feeds purified water to the points of use. Some systems employ a return line from the points of use back to the inlet of the purification process. This allows circulation of the water when not called upon by the points of use. Typically, in this type of design, the demand rate at the point of use is determined. The systems production rate is designed to meet this demand with an additional 10–20 percent. This invention employs a different concept from the prior art. The design of this invention is to provide purified water where required (point of use) but as a direct draw off point within the high purity side of the inventions purification process. Water obtained is a direct draw of freshly purified water from the invention. Unlike the prior art, the piping to the use point and return to the membrane assembly is an integral part of the purification process. The production rate of the invention is typically twice that of the draw off demand. The hydraulic conditions are different from the prior art in order to maintain the velocities within the purification process. In addition, the low total dissolved solids, water and carbon dioxide balance is required in the volume of water that is returned to the membrane assembly on a continuous basis.

Figure 7:
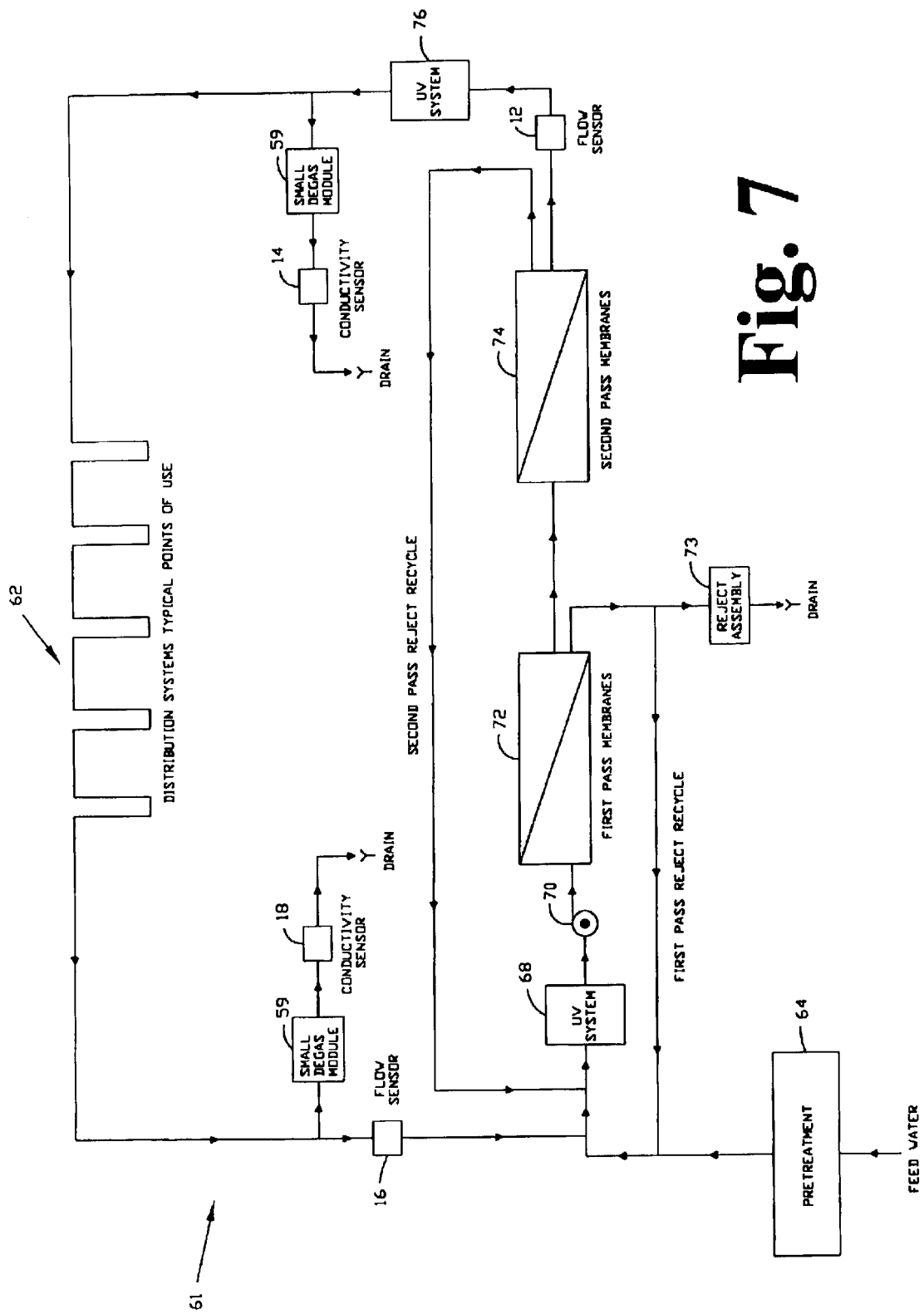
FIG. 7 is a schematic flow diagram showing a water purification system according to the invention which is similar to the system drawn in FIG. 2 but which includes small degasification modules for sampling a fraction of product water.

The natural state of the system is to run it without pH adjustment to derive the benefits of the $CO_2$ in the production and circulation mode. The conductivity of the product water will be elevated due to the dissolved $CO_2$ gas, which forms carbonic acid and in turn contributes to conductivity. In applications where a specified conductivity is to be maintained for the reason of determining the maximum allowable total dissolved solids content without the interference of the conductivity contributed by $CO_2$, the $CO_2$ gas can be removed on a low volume product sample stream. A sample stream of the product water from either the outlet of the second pass membranes before the loop, or water returning back from the loop, or both places, can be passed through a small degas membrane module 59 (e.g. Liqui-Cel by Celgard or similar) prior to a conductivity sensor 14, 18 as shown in the water purification system 61 of FIG. 7. The conductivity sensor 14, 18 would then register only the conductivity contributed by the total dissolved solids (i.e. USP Stage 1 online conductivity analysis).

Where a requirement exists to produce water of a reduced conductivity, sodium hydroxide or other suitable alkali can be added to the feed water at 66 to convert the $CO_2$ to carbonate, which will be rejected by the membranes, producing lower conductivity product water. Suitable systems for pH adjustment under variable flow conditions are commercially available such as those manufactured by Prominent Fluid Controls. In this case, a softener would be required in the pretreatment to prevent a more rapid scaling of the membranes under alkaline conditions. Under these conditions, a timing mechanism or a manual turning off of the NaOH injection pump 66 will produce a low pH in the system and distribution loop to achieve self cleaning and sanitizing, during off hours of production. This state can also be achieved between draw off requirements during normal production. The normal state will be to maintain a low pH. When water is required, a switch by the points of use will activate the NaOH pump 66 to bring the pH to within the desired range (approximately 8.3 on the first pass membranes) in order to provide water of a lower conductivity. After draw down, the NaOH pump 66 is once again turned off to maintain an acid cleaning and sanitizing state.

Figure 8:
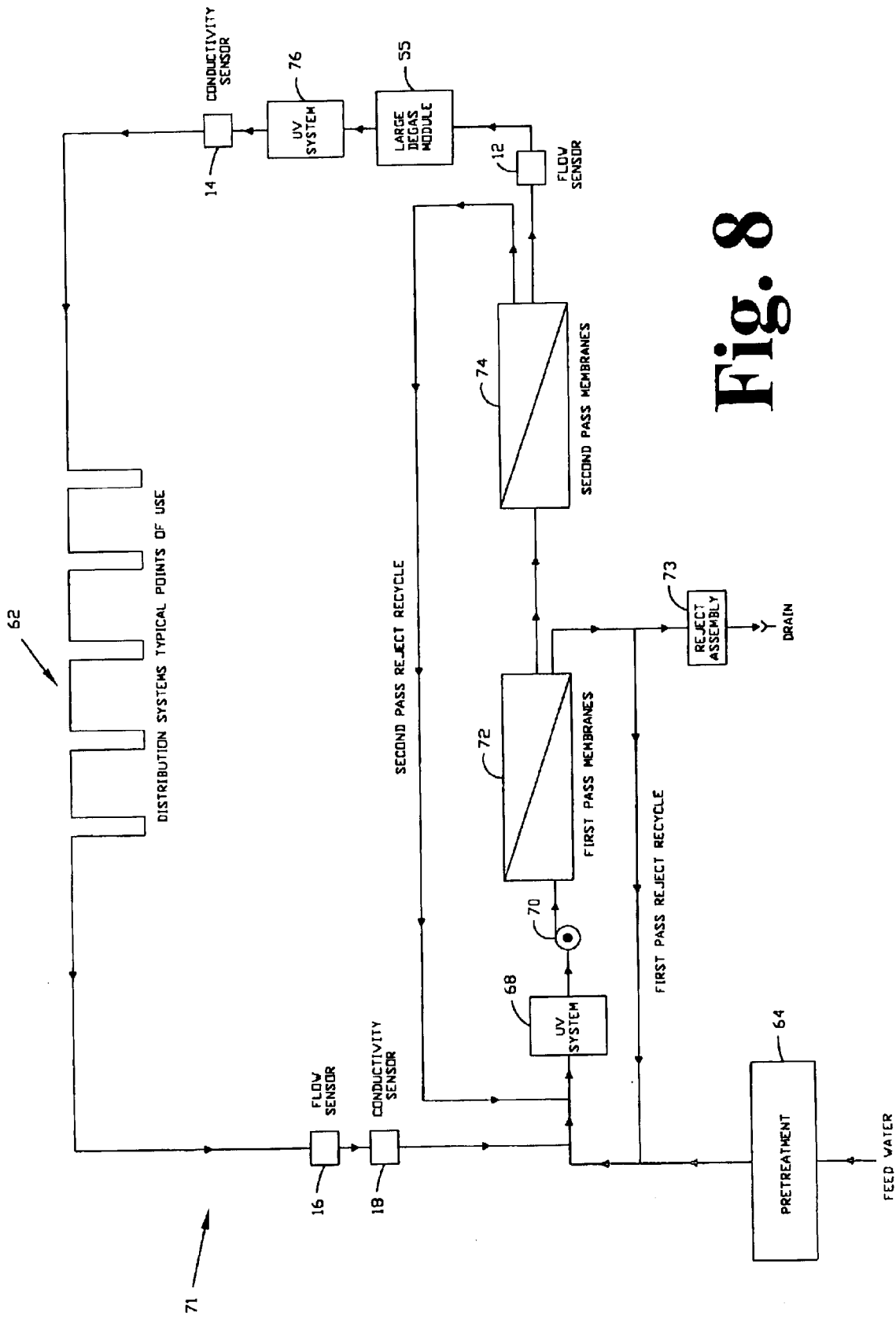
FIG. 8 is a schematic flow diagram showing a water purification system according to the invention which is similar to the system drawn in FIG. 2 but which includes a large degasification module for removing $CO_2$ from all of the product water.

Alternatively, the $CO_2$ gas can be removed from the water, by incorporating a carbon dioxide degassing module such as a membrane contactor (e.g. Liqui-Cel by Celgard or similar) to increase the pH back to a specified and desired value and also to reduce conductivity at the points of use, as required. A membrane contactor 55, placed on the permeate side of the second pass, prior to the ultraviolet radiation treatment, will remove the $CO_2$ gas as shown in the water purification system 71 of FIG. 8. The removal of the gas will reduce the conductivity and increase the pH back to the specified and desired value. The degas module can be connected to a sweep gas source or a vacuum can be drawn on the module to remove the $CO_2$ from the product water. Another alternative is to allow the gas to escape from the purified water after drawing it from the system. Once the pressure has been released, the $CO_2$ will naturally evolve from the water decreasing the conductivity and increasing the pH.

Figure 9:
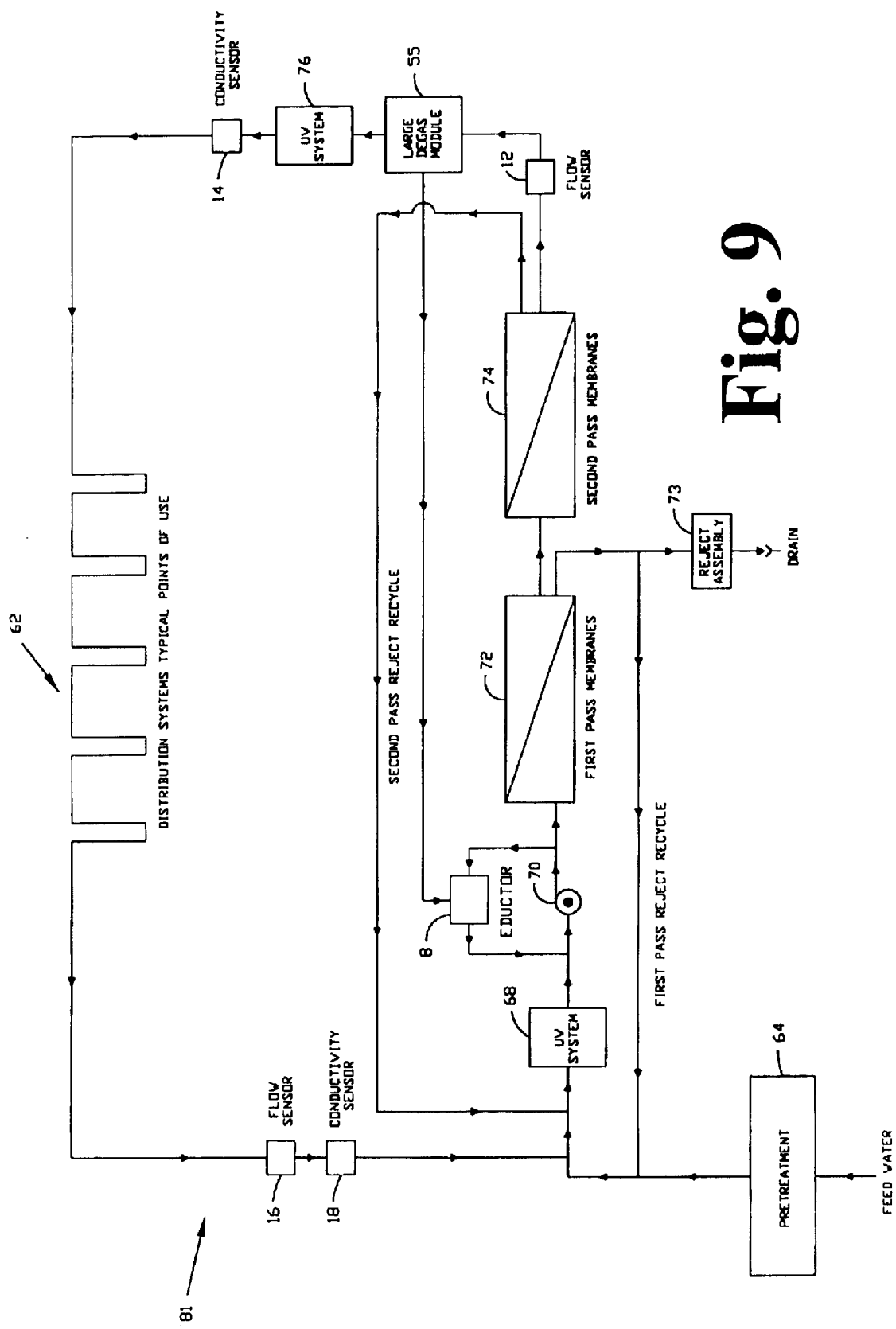
FIG. 9 is a schematic flow diagram showing a water purification system according to the invention which is similar to the system drawn in FIG. 2 but which includes a large degasification module for removing $CO_2$ from all of the product water in association with an eductor for returning $CO_2$ into the system upstream from a first reverse osmosis membrane assembly.

Another alternative system 81 shown in FIG. 9 is to use an eductor 8 connected to a membrane contactor, which is located after the second pass and prior to the ultraviolet system. An eductor 8, placed on a water line from the discharge of the pump 70 and connected to the inlet of the pump, and having the vacuum line of the eductor connected to the membrane contactor 55 removes $CO_2$ gas from the product water and introduces it to the feed water. This will reduce the alkalinity in the feed water, reducing scaling of the membranes and reducing pH within the system prior to the contactor to prevent microbial growth Where the points of use require hot water or the membrane selected for use in the reverse osmosis membrane assemblies 72, 74 are operated at higher temperatures (70–80° C.), continuously or periodically to kill bacteria, the ultraviolet radiation systems 68 and 76 may be replaced by heat exchangers identified by reference numerals 78, 80 respectively in the embodiment of a water purification system 82 shown in FIG. 3. The remaining components are otherwise similar to those in the water purification system 60 of FIG. 2 and are identified by like numerals. The second optional heat exchanger 80 is disposed to control the temperature of the permeate before reaching the points of use indicated at 62 to increase or maintain high water temperatures, for example, in water for injection purposes, to cool the water for other end uses, or to sanitize the loop and associated equipment attached to the point of use loop. In such systems, it will be appreciated that operating costs will be higher because of the energy costs associated with heating water. Therefore, the aforementioned operating cost advantages described with reference to FIG. 2 will be reduced.

Figure 3:
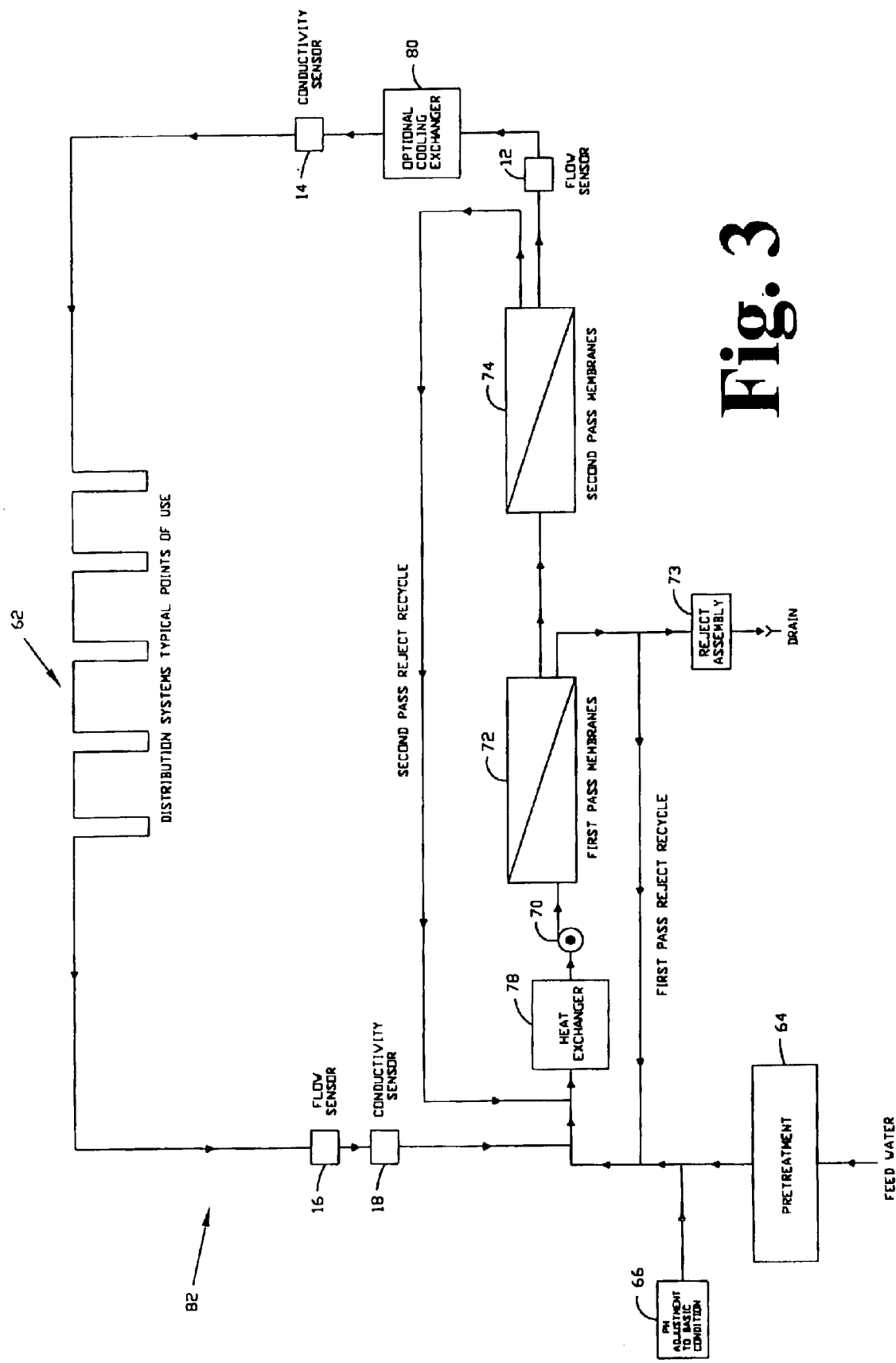
FIG. 3 is a schematic flow diagram showing a water purification system according to the invention and including a double pass reverse osmosis membrane assembly with points of use and operating at a hot temperature, or to be operated cold and to be periodically hot water sanitized.
Figure 4:
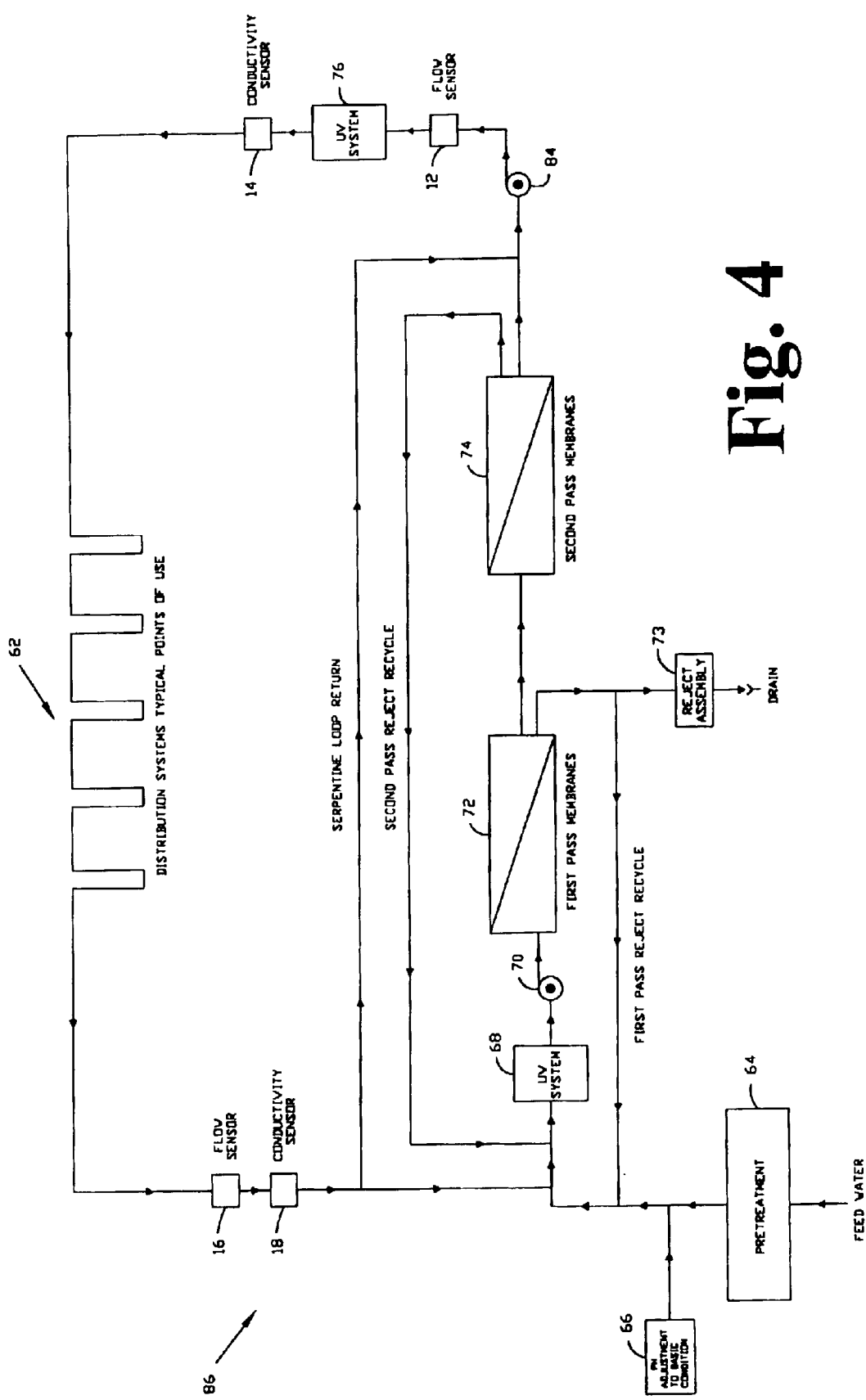
FIG. 4 is a schematic flow diagram showing a water purification system according to the invention and including a double pass reverse osmosis membrane assembly with points of use and operating at a cold temperature and having a serpentine loop return after the purification system for continuous circulation in the loop.
Figure 5:
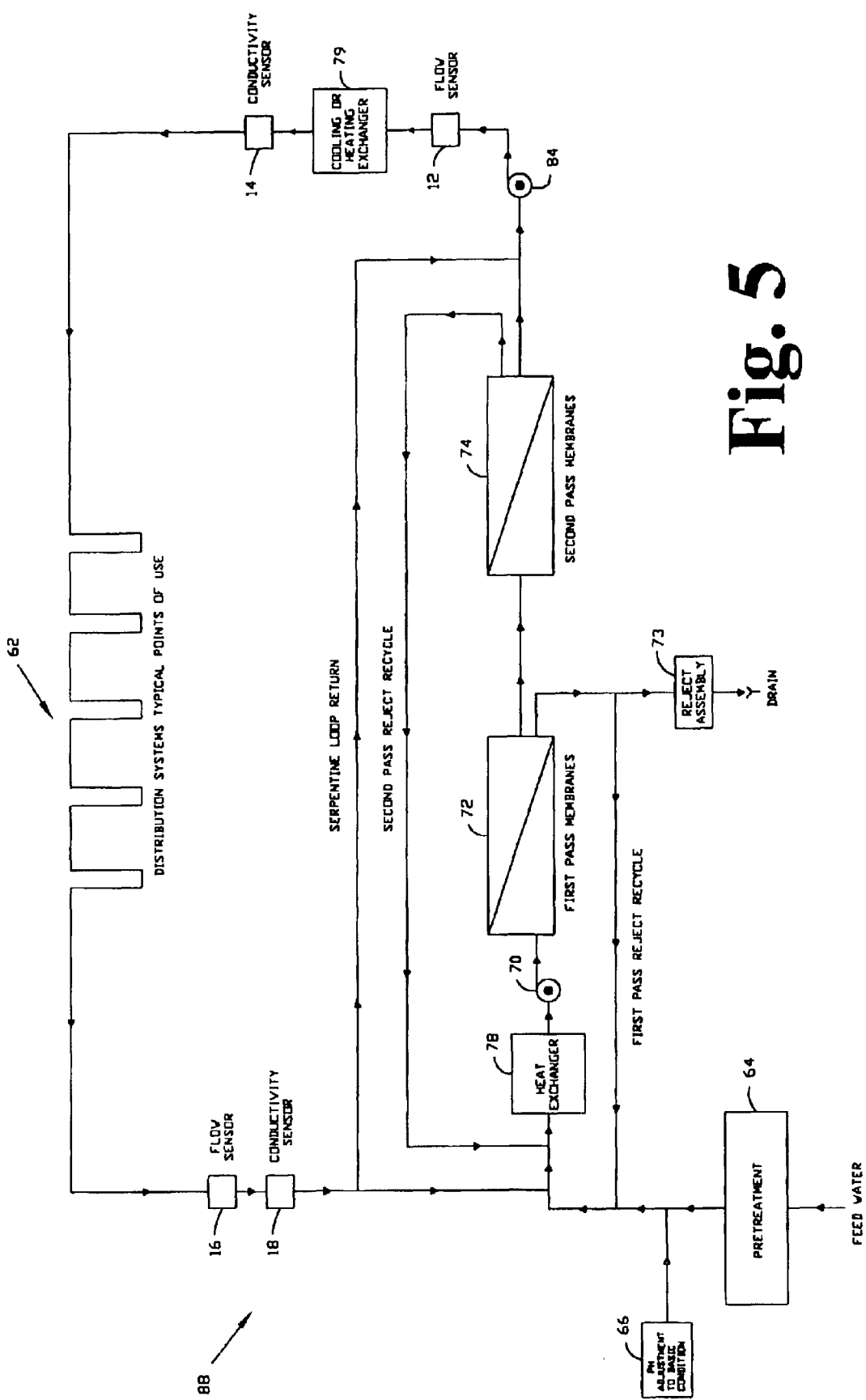
FIG. 5 is a schematic flow diagram showing a water purification system according to the invention and including a double pass reverse osmosis membrane assembly with points of use and operating at a hot temperature and having a serpentine loop return for recirculated excess permeate not used at points of use.

Both systems 60 and 82 of FIGS. 2 and 3 may be modified to create systems 86, 88 as shown in FIGS. 4 and 5 in which a serpentine loop return is added in which permeate is drawn through pump 84 disposed to bypass both the first and second reverse osmosis membrane assemblies 72, 74. Placing the systems 86, 88 on standby, where pump 70 is operated for a few minutes every hour, to flush the systems, will reduce overall water requirements to conserve water while maintaining a minimum velocity of water in the point of use piping that inhibits the formation of biofilm and prevents water stagnation.

Figure 6:
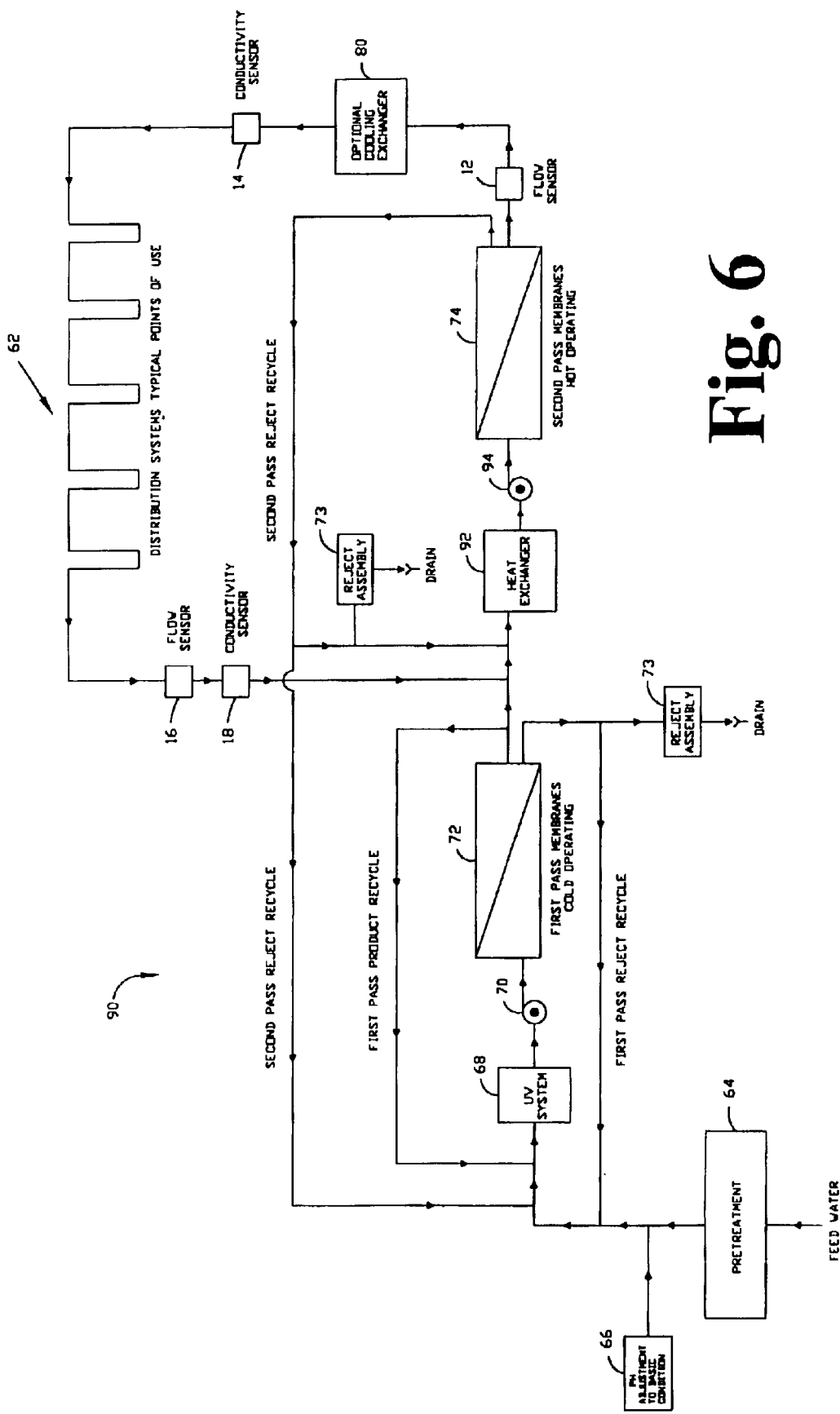
FIG. 6 is a schematic flow diagram showing a water purification system according to the invention and including a double pass reverse osmosis membrane assembly with points of use and operating at both hot and cold temperatures.

A hybrid system 90 of systems 60 and 82 is illustrated in FIG. 6 where the first reverse osmosis membrane assembly 72 is operated at a cold temperature and is associated with an upstream ultraviolet radiation station 68 and the second reverse osmosis membrane assembly 74 is operated at an elevated temperature and is associated with an upstream heat exchanger 92 and pump 94 disposed between the first reverse osmosis membrane assembly 72 and the second reverse osmosis membrane assembly 74. A second optional heat exchanger 80 is disposed to control the temperature of the permeate before reaching the points of use indicated at 62.

It will be seen that the permeate from the second reverse osmosis membrane assembly 74 is drawn by the pump 94 to return through the heat exchanger 92 into the second reverse osmosis membrane assembly 74 while the reject water from the second pass reverse osmosis membrane assembly 74 is divided into two fractions supplying both the first and second pass reverse osmosis membrane assemblies 72, 74.

The permeate from the first pass reverse osmosis membrane assembly 72 also has a fraction which is recycled through the ultraviolet radiation station 68 and its reject water is divided into two fractions, one of which goes to drain while the other is recycled through the ultraviolet radiation station 68.

In use, it will be appreciated that a water purification system built in accordance with the invention provides enormous cost benefits. The capital costs are significantly lower, providing savings in the order of 30 to 50% over prior art systems which include a water storage tank. Operating costs are also reduced by 20 to 50%, the savings being attributable to lower energy consumption and reduced labour for cleaning and sanitizing. Most advantageously, a system built in accordance with the invention produces water of high microbiological purity without the infrastructure associated with hot water sanitization and ozone sanitization.

What is claimed is:

1. A water purification system having:
   a feed water inlet;
   a first pass reverse osmosis filter assembly receiving feed water from the feed water inlet;
   a second pass reverse osmosis filter assembly receiving purified water from the first pass reverse osmosis filter assembly producing further purified water;
   a purified water distribution system for distributing purified water to points of use, the purified water distribution system being coupled to said reverse osmosis filter assemblies without any intermediate water storage, and being adapted to return purified water to at least one of said reverse osmosis filter assemblies to continuously purify the water and ensure microbiological purity in said purified water, the purified water distribution system including a variable speed pump for creating sufficient water pressure in the distribution system to maintain carbon dioxide in solution and produce an acidic environment; and
   a reject water distribution system for returning reject water from the first pass reverse osmosis filter assembly and the second pass reverse osmosis filter assembly to the first pass reverse osmosis filter assembly.

2. A water purification system according to claim 1, wherein the system is operable to produce further purified water having a reduced pH of below 7.0.

3. A water purification system according to claim 2 having a first ultraviolet radiation treatment system disposed to treat water entering the first pass reverse osmosis fitter assembly and having a second ultraviolet radiation treatment system disposed to treat purified water leaving the second pass reverse osmosis filter assembly.

4. A water purification system according to claim 2 having a first heat exchanger disposed to treat water entering the first pass reverse osmosis filter assembly.

5. A water purification system according to claim 4 having a second heat exchanger disposed to treat water exiting the second pass reverse osmosis filter assembly.

6. A water purification system according to claim 2 in which the purified water distribution system is adapted to return purified water to the first pass reverse osmosis filter assembly.

7. A water purification system according to claim 2 in which the purified water distribution system is adapted to return a portion of purified water to an outlet exiting from the second pass reverse osmosis filter assembly.

8. A water purification system according to claim 2 in which the reject water distribution system is adapted to return a portion of the reject water from the second pass reverse osmosis filter assembly to the second pass reverse osmosis filter assembly.

9. A water purification system according to claim 8 in which the purified water distribution system is adapted to return purified water to the second pass reverse osmosis filter assembly.

10. A water purification system according to claim 2 having means for pH adjustment of the purified water leaving the second pass reverse osmosis filter assembly, said means for pH adjustment being adapted to remove carbon dioxide gas from the purified water.

11. A water purification system according to claim 10 additionally including an eductor coupled to said means for pH adjustment and to a pump for returning carbon dioxide gas into a feed water supply to said first pass reverse osmosis meter assembly.

12. A method of operating a water purification system according to claim 2 in which feed water flow rate to the first pass reverse osmosis assembly is at least three times an average production rate from the second pass osmosis assembly to reduce fouling of the reverse osmosis membranes in said first pass reverse osmosis assembly.

13. A method of operating a water purification system according to claim 2 in which the pH of water feeding the first pass reverse osmosis assembly is maintained below 7.0 during an idle or circulation mode to self clean the membranes.

14. A water purification system according to claim 1 having a flow sensor for monitoring water flow rate in the purified water distribution system and coupled to the variable speed pump to maintain a minimum average water velocity of 3 ft/sec (1 meter/sec) in the purified water distribution system whereby the growth of microorganisms and information of biofilm is minimized.

15. A water purification system according to claim 1 having a sensor to measure water conductivity and temperature and coupled to a value for releasing reject water from the system when conductivity and temperature specifications are exceeded.

16. A water purification system according to claim 1 having means for pH adjustment of the feed water disposed to treat water entering said at least one reverse osmosis filter assembly to regulate the pH and conductivity of purified water exiting said at least one reverse osmosis filter assembly.

17. A water purification system according to claim 16 having sodium hydroxide addition means for adding sodium hydroxide to the feed water.

18. A water purification system according to claim 1 having water sampling means for removing carbon dioxide from a sample stream of purified water upstream from a conductivity sensor.

19. A water purification system according to claim 1 in which the pump has a self-regulating range to vary production rates of purified water between 50 and 150% of a nominal production rate in response to purified water demand at points of use.

20. A water purification system according to claim 1 in which the pump is manually operable to vary production rates of purified water between 50 and 150% of a nominal production rate in response to purified water demands at points of use.

21. A method of operating a water purification system according to claim 1 in which minimum velocity of 3 ft/sec (1 meter/sec) is maintained in the purified water distribution system to produce turbulent flow conditions which discourage contamination from microorganisms.

22. A method of operating a water purification system according to claim 1 in which the pH of the purified water is maintained below 5.5 during an idle mode of operation to ensure microbiological purity in the purified water.

23. A method of operating a water purification system according to claim 1 in which the pump is adapted to regulate production rates of purified water through said at least one reverse osmosis filter assembly in response to purified water demand at points of use.

24. A method of operating a water purification system according to claim 1 in which the system is operated continuously so that water is never left stagnant.

25. A water purification system having
a feed water inlet;
a first pass reverse osmosis filter assembly for receiving feed water from the feed water inlet and a second pass reverse osmosis filter assembly for receiving purified water from the first pass reverse osmosis filter assembly, the second pass reverse osmosis filter assembly being adapted to produce purified water having a reduced pH of below 7.0,
a reject water distribution system for returning reject water from the first pass reverse osmosis filter assembly and the second pass reverse osmosis filter assembly to the first pass reverse osmosis filter assembly,
a purified water distribution system for distributing purified water to points of use, the purified water distribution system being coupled to said reverse osmosis filter assemblies without any intermediate water storage, and being adapted to return purified water to said first pass reverse osmosis filter assembly to continuously purify the water and ensure microbiological purity in said purified water, the purified water distribution system including a variable speed pump for creating sufficient water pressure in the distribution system to maintain carbon dioxide in solution and produce an acidic environment;
means for pH and conductivity adjustment of the purified water leaving the second pass reverse osmosis filter assembly, said means for pH adjustment being adapted remove carbon dioxide gas from the purified water; and
an eductor coupled to said means for pH adjustment and to the pump for returning carbon dioxide gas into a feed water supply to said first reverse osmosis meter assembly.

26. A water purification system having:
a feed water inlet;
a first pass reverse osmosis filter assembly receiving feed water from the feed water inlet;
a second pass reverse osmosis filter assembly receiving purified water from the first pass reverse osmosis filter assembly producing further purified water;
a purified water distribution system for distributing purified water to points of use, the purified water distribution system being coupled to said reverse osmosis filter assemblies without any intermediate water storage, and being adapted to return purified water to at least one of said reverse osmosis filter assemblies to continuously purify the water and ensure microbiological purity in said purified water, the purified water distribution system including means for creating sufficient water pressure in the distribution system to maintain carbon dioxide in solution and produce an acidic environment; and a reject water distribution system for returning reject water from the first pass reverse osmosis filter assembly and the second pass reverse osmosis filter assembly to the first pass reverse osmosis filter assembly.

27. A water purification system according to claim 26, wherein the system is operable to produce purified water having a reduced pH of below 7.

28. A method of operating a water purification system according to claim 26 in which minimum velocity of 3 ft/sec (1 meter/sec) is maintained in the purified water distribution system to produce turbulent flow conditions which discourage contamination from microorganisms.

* * * * *

UNITED STATES PATENT AND TRADEMARK OFFICE
CERTIFICATE OF CORRECTION

PATENT NO. : 6,908,546 B2
APPLICATION NO. : 10/285621
DATED : June 21, 2005
INVENTOR(S) : Steven D. Smith It is certified that error appears in the above-identified patent and that said Letters Patent is hereby corrected as shown below:

On Title Page, Item (54) Col. 1,
The title should read: --Apparatus and Method for Producing Purified Water Having High Microbiological Purity--

Column 3, lines 8-10 should be deleted.

Claim 3, column 14 line 54, "fitter" should read --filter--.

Claim 14, column 15 line 39, "information" should read --formation--.

Claim 15, column 15 line 42, "value" should read --valve--.

Signed and Sealed this

Eighth Day of August, 2006

JON W. DUDAS
*Director of the United States Patent and Trademark Office*